United States Patent
Chen et al.

(10) Patent No.: US 9,714,906 B2
(45) Date of Patent: Jul. 25, 2017

(54) NUCLIDE IDENTIFICATION METHOD, NUCLIDE IDENTIFICATION SYSTEM, AND PHOTONEUTRON EMITTER

(71) Applicants: TSINGHUA UNIVERSITY, Beijing (CN); NUCTECH COMPANY LIMITED, Beijing (CN)

(72) Inventors: Zhiqiang Chen, Beijing (CN); Yigang Yang, Beijing (CN); Xuewu Wang, Beijing (CN); Qinjian Zhang, Beijing (CN); Huaibi Chen, Beijing (CN); Yuanjing Li, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 36 days.

(21) Appl. No.: 14/577,701

(22) Filed: Dec. 19, 2014

(65) Prior Publication Data
US 2015/0185164 A1 Jul. 2, 2015

(30) Foreign Application Priority Data
Dec. 27, 2013 (CN) .......................... 2013 1 0740973

(51) Int. Cl.
*G01N 23/00* (2006.01)
*G21G 4/02* (2006.01)
*G01V 5/00* (2006.01)

(52) U.S. Cl.
CPC ......... *G01N 23/005* (2013.01); *G01V 5/0091* (2013.01); *G21G 4/02* (2013.01)

(58) Field of Classification Search
CPC ....... G01N 23/005; G21G 4/02; G01V 5/0091
See application file for complete search history.

(56) References Cited

U.S. PATENT DOCUMENTS

2009/0074128 A1* 3/2009 Bertozzi ............. G01V 5/0091
376/170
2010/0201240 A1* 8/2010 Heinke .................... H05H 9/00
313/35

(Continued)

FOREIGN PATENT DOCUMENTS

CN          1959387 A       5/2007
CN       201286191 Y        8/2009

(Continued)

*Primary Examiner* — David Porta
*Assistant Examiner* — Mindy Vu
(74) *Attorney, Agent, or Firm* — Oliff PLC

(57) ABSTRACT

Embodiments of the present invention disclose a nuclide identification method, a nuclide identification system, and a photoneutron emitter. The photoneutron emitter comprises: a pulsed electron accelerator configured for emitting electrons; and a photoneutron converting target configured to receive the electrons emitted by the pulsed electron accelerator and convert the electrons into photoneutrons. The photoneutron converting target has a volume of about 100 to about 8000 $cm^3$, of about 100 to about 2500 $cm^3$, or of about 785 $cm^3$. These embodiments of the present invention can improve an accuracy of identification of a nuclide, and provide a practical photoneutron emitter, method and system for identifying a nuclide. Especially, these embodiments of the present invention can improve an accuracy of identification of a fissile nuclide such as $^{233}U$, $^{235}U$, and $^{239}Pu$, and provide a practical photoneutron emitter, method and system for identifying a fissile nuclide such as $^{233}U$, $^{235}U$, and $^{239}Pu$.

18 Claims, 3 Drawing Sheets

(56) References Cited

U.S. PATENT DOCUMENTS

| 2011/0096886 A1* | 4/2011 | Kang | G01V 5/0091 |
| | | | 376/154 |
| 2014/0029709 A1* | 1/2014 | Gahl | H05H 3/06 |
| | | | 376/114 |
| 2014/0270034 A1* | 9/2014 | Clayton | G01V 5/0091 |
| | | | 376/154 |

FOREIGN PATENT DOCUMENTS

| CN | 101581679 A | 11/2009 |
| CN | 103314311 A | 9/2013 |
| CN | 203801141 U | 8/2014 |
| JP | 2006-010356 A | 1/2006 |
| JP | 2010-210452 A | 9/2010 |
| JP | 2013-130418 A | 7/2013 |

\* cited by examiner

NUCLIDE IDENTIFICATION METHOD, NUCLIDE IDENTIFICATION SYSTEM, AND PHOTONEUTRON EMITTER

CROSS-REFERENCE TO RELATED APPLICATION

This application claims the benefit of Chinese Patent Application No. 201310740973.4 filed on Dec. 27, 2013 in the State Intellectual Property Office of China, the whole disclosure of which is incorporated herein by reference.

BACKGROUND OF THE INVENTION

1. Field of the Invention

Embodiments of the present invention relate to a nuclide identification method, a nuclide identification system, and a photoneutron emitter for identifying a nuclide, and in particular, to a method, a system, and a photoneutron emitter which are configured to identify a fissile nuclide such as $^{233}$U, $^{235}$U, and $^{239}$Pu.

2. Description of the Related Art

In safety inspection, it is very important to inspect a fissile nuclide. The so-called fissile nuclide mainly indicates nuclides, such as $^{233}$U, $^{235}$U, and $^{239}$Pu, that can be induced to split by thermal neutrons.

SUMMARY OF THE INVENTION

In accordance with an embodiment of the present invention, there is provided a photoneutron emitter for identifying a nuclide. The photoneutron emitter comprises: a pulsed electron accelerator configured for emitting electrons; and a photoneutron converting target configured to receive the electrons emitted by the pulsed electron accelerator and convert the electrons into photoneutrons.

In accordance with an embodiment of the present invention, there is provided a nuclide identification method comprising the steps of: placing an object to be inspected between a photoneutron emitter and a photoneutron detector; emitting, by the photoneutron emitter, photoneutrons having a predetermined range of energy at a predetermined time;

detecting, by the photoneutron detector, a plurality of quantities of the photoneutrons which respectively fly to the photoneutron detector for different times of flight, so as to acquire a sample spectrum in which the plurality of quantities of the photoneutrons are ordered according to the different times of flight; and determining a nuclide contained in the object based on whether or not the quantity of the photoneutrons within a particular range of time of flight in the sample spectrum is lower than a predetermined value.

In accordance with an embodiment of the present invention, there is provided a nuclide identification system comprising:

a photoneutron emitter configured for emitting photoneutrons having a predetermined range of energy at a predetermined time;

a photoneutron detector configured for receiving the photoneutrons emitted by the photoneutron emitter to acquire a plurality of quantities of the photoneutrons received at respective times;

a photoneutron time-of-flight timer configured for recording times of flight, of the photoneutrons emitted by the photoneutron emitter, from a time of being emitted to times of being received by the photoneutron detector; and a data processing unit configured for forming a photoneutron quantity spectrum in which the plurality of quantities of the photoneutrons are ordered according to the times of flight, based on the quantity of the photoneutrons received by the photoneutron detector at every time, and the times of flight.

DETAILED DESCRIPTION OF THE EMBODIMENTS

Figure 1:
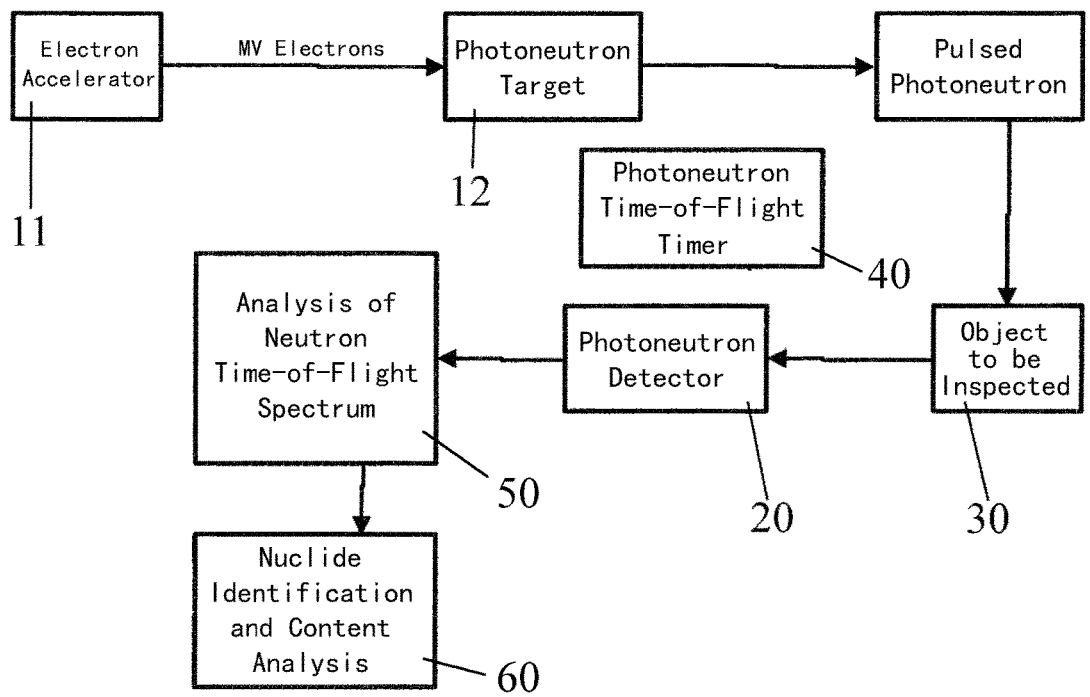
FIG. 1 is a principle diagram of a nuclide identification method according to an embodiment of the present invention.

A further description of the invention will be made as below with reference to embodiments of the present invention taken in conjunction with the accompanying drawings.

As shown in FIGS. 1-4, a nuclide identification system according to an embodiment of the present invention comprises: a photoneutron emitter 10, a photoneutron detector 20, a photoneutron time-of-flight timer 40, and a data processing unit (Analysis of Neutron Time-of-Flight Spectrum) 50. The photoneutron emitter is configured to emit photoneutrons having a predetermined range of energy at a predetermined time, and the photoneutron detector is configured to receive the photoneutrons emitted by the photoneutron emitter to acquire a plurality of quantities of the photoneutrons received at respective times. The photoneutron time-of-flight timer 40 is configured to record times of flight, of the photoneutrons emitted by the photoneutron emitter, from a time of being emitted to times of being received by the photoneutron detector 20. The data processing unit 50 is configured to form a photoneutron quantity spectrum in which the plurality of quantities of the photoneutrons are ordered according to the times of flight, based on the quantity of the photoneutrons received by the photoneutron detector 20 at every time, and the times of flight (referring to FIG. 4). The nuclide identification system may further comprise a comparison and determination unit (Nuclide Identification and Content Analysis) 60 for determining a nuclide contained in an object to be inspected by comparing a quantity of the photoneutrons, within a particular range of time of flight in a photoneutron quantity spectrum acquired when the object is placed between the photoneutron emitter and the photoneutron detector, with a predetermined value. The nuclide identification system according to the embodiment of the present invention can be used to identify a fissile nuclide such as $^{233}$U, $^{235}$U, and $^{239}$Pu.

The comparison and determination unit 60 may determine whether or not the quantity of the photoneutrons within the particular range of time of flight in the photoneutron quantity spectrum acquired when the object is placed is lower than the predetermined value, by comparing the photoneutron quantity spectrum, acquired when the object is placed, with a photoneutron quantity spectrum acquired when no object is placed. In addition, the predetermined value may be determined in any other way. For example, the predetermined value may be determined according to theoretical data and empirical data.

The operational principle of the nuclide identification system according to the embodiment of the present invention is as follows.

1. Neutron Resonance

Any physical particle has the wave-particle duality, and the neutrons are naturally no exception. A target nucleus (such as $^{235}$U and $^{238}$U described herein) has undulatory property as its main characteristic when energies of the neutrons are not very high. Since a nuclear force is strong and short in distance, there is a very large difference of kinetic energies of the neutrons before and after the neutrons enter the target nucleus (the former is large and the latter is small). Generally, an enormous change in wave length of the neutrons occurring at a boundary of the target nucleus necessarily causes a probability that the neutrons enter the target nucleus to degrade greatly, which is reflected by the fact that a scattering section of the neutrons is not great. However, when the kinetic energies of the neutrons are under some particular values, a wave function of the neutrons inside the target nucleus has a phase of $\pi/2$ at the boundary of the target nucleus. In this case, an amplitude of the wave function of the neutrons inside the target nucleus is the same as an amplitude of the wave function of the neutrons outside the target nucleus, which is reflected by the fact that the scattering section of the neutrons reaches a local maximum. This is the resonance phenomenon.

Figure 2:
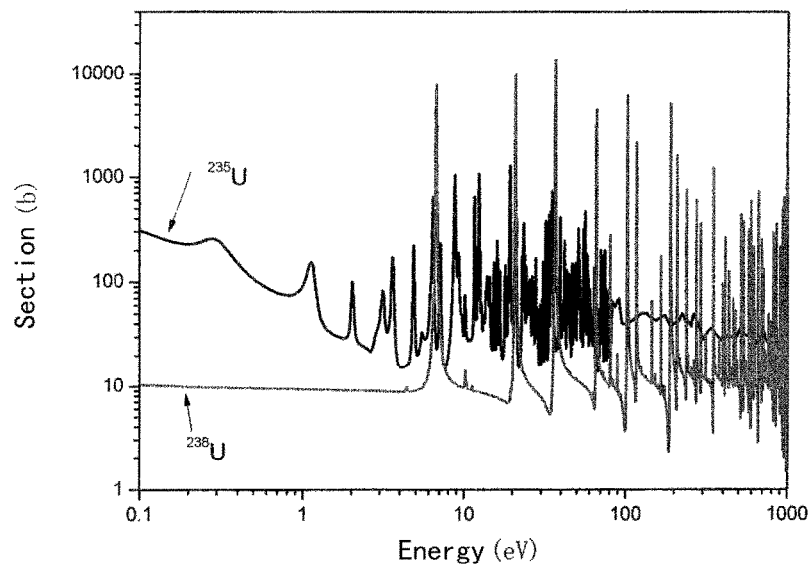
FIG. 2 is a diagram showing neutron nelastic scattering curves of $^{235}$U and $^{238}$U.

It can be seen from the above description that, the resonance occurs after the incident neutrons act together with nucleons in the atomic nucleus when the energies of the incident neutrons reach some particular values. Therefore, if the resonance occurs, the energies of the neutrons are very correlative with which the target nucleus is. In short, if the resonance occurs, the energies of the neutrons are completely correlative with the nuclide of the target nucleus. If we know a position of a resonant scattering energy of a nuclide, we can learn which the nuclide is by analysis. FIG. 2 shows neutron nelastic scattering curves of $^{235}$U and $^{238}$U. It can be seen that resonant scattering of $^{235}$U occurs at 0.28 eV, 1.13 eV, 2 eV, and the like, while resonant scattering of $^{238}$U occurs at 6.67 eV, 20.9 eV and the like.

In order that $^{235}$U and $^{238}$U can be analyzed by the resonant scattering, it is necessary that a range of energies of the neutrons meets the requirements as shown in FIG. 2. For example, the energies of the neutrons are in a range of 0.1 eV to 1 keV. If such neutrons are used to penetrate a material to be inspected, a nuclide can be identified by a position of a resonance hump by analyzing an energy spectrum of the transmitted neutrons. However, it is well known that it is very difficult to directly measure the energies of the neutrons. Time-of-flight (TOF) technique can be used to analyze the energies of the neutrons in the range of 0.1 eV to 1 keV.

2. Time-of-Flight Technique

Figure 3:
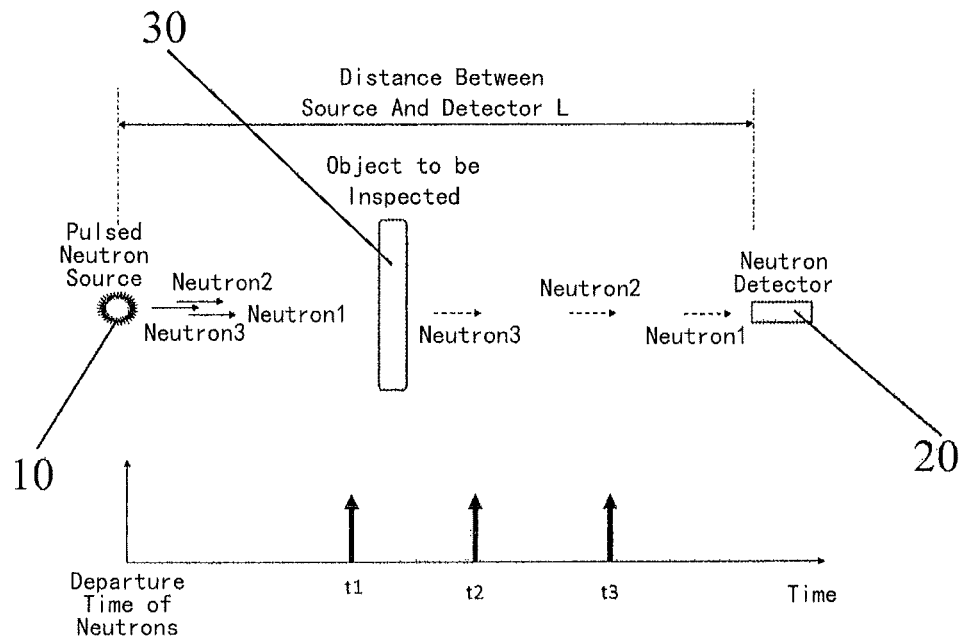
FIG. 3 is a schematic diagram of a nuclide identification system according to an embodiment of the present invention.
Figure 4:
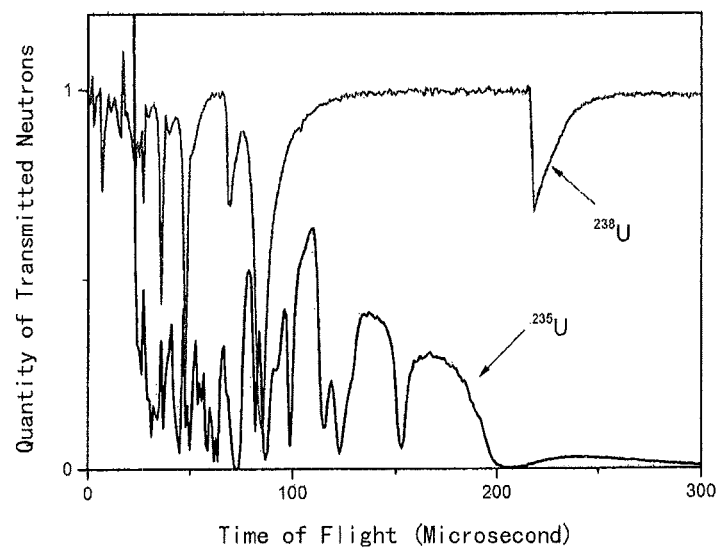
FIG. 4 is a diagram showing time-of-flight spectrums of $^{235}$U and $^{238}$U when they are respectively detected.

If departure time of the neutrons is given, times of flight of the neutrons can be used to calculate the energies of the neutrons. FIG. 3 is a schematic diagram showing a principle. A neutron source 10 shown in FIG. 3 is a pulsed source. The neutron source 10 emits a plurality of neutrons (such as neutrons 1, 2, and 3) at a same time (such as the departure time of the neutrons). Times for which the three neutrons fly to the detector 20 are different from one another due to their different speeds. As shown in FIG. 3, the three neutrons 1, 2, and 3 arrive at the detector 20 at the times t1, t2, and t3, respectively. Since a distance L between the neutron source 10 and the detector 20 is definite, the speeds of the neutrons and thus the energies of the neutrons can be calculated according to the times t1-t3 and the distance L. If a substance 30 to be detected is added to a flight path of the neutrons and resonant scattering occurs between the neutrons and a nuclide in the substance 30, a chance of the neutrons, at a position of a resonant scattering energy, to be detected by the detector 20 will be considerably decreased. A quantity of the neutrons to be detected by the detector 20 at the time t, which corresponds to the resonant scattering energy and which is equal to a sum of the departure time of the neutrons and the time of flight, will be accordingly decreased. By analyzing where the quantity of the neutrons detected by the detector 20 are considerably decreased in the time spectrum, it can be inversely derived the neutrons of which energy are resonantly scattered and thus it is learned which the nuclide is. FIG. 4 shows a calculation result (assuming that the energy spectrum of incident neutrons is a white spectrum).

It can be seen from FIG. 4 that $^{235}$U and $^{238}$U have different transmission characteristics and owns completely different resonant attenuation positions in the time spectrum. Thereby, $^{235}$U and $^{238}$U can be identified.

In order to achieve the effect as shown in FIG. 4, the energy of the neutron source 10 may be in a range of 0.1 eV to 1 keV. Furthermore, the neutrons should have a definite departure time. Only in this way can the time-of-flight spectrum begin to be measured. In addition, since the resonance occurs within a narrow range of energy, the neutron source needs to be large in yield in order to improve analysis sensitivity.

A nuclide identification method according to an embodiment of the present invention will be described below. The nuclide identification method can be used to identify a fissile nuclide such as $^{233}$U, $^{235}$U, and $^{239}$Pu.

Referring to FIGS. 1 and 3, firstly, an object 30 to be inspected is placed between a photoneutron emitter 10 and a photoneutron detector 20, and photoneutrons having a predetermined range of energy are emitted by the photoneutron emitter 10 at a predetermined time. Then, a plurality of quantities of the photoneutrons which respectively fly to the photoneutron detector 20 for different times of flight are detected by the photoneutron detector 20, so as to acquire a sample spectrum in which the plurality of quantities of the photoneutrons are ordered according to the different times of flight, as shown in FIG. 4. Next, a nuclide contained in the object is determined based on whether or not, in the sample spectrum, the quantity of the photoneutrons within a particular range of time of flight is lower than a predetermined value. For example, as shown in FIG. 4, the photoneutrons corresponding to a particular time of flight are absorbed and thus decrease in number. Thereby, a corresponding nuclide contained in the object can be judged.

Furthermore, according to the method in the embodiment, provided that no object is placed, photoneutrons having the predetermined range of energy are emitted by the photoneutron emitter 10 at a predetermined time, and a plurality of quantities of the photoneutrons which respectively fly to the photoneutron detector 20 for different times of flight are detected by the photoneutron detector 20, thereby acquiring a standard spectrum in which the plurality of quantities of the photoneutrons are ordered according to the different times of flight. By comparison of the sample spectrum with the standard spectrum as a reference, it is determined whether or not, in the sample spectrum, the quantity of the photoneutrons within the particular range of time of flight is lower than the predetermined value.

In addition, for example, as shown in FIG. 4, the photoneutrons corresponding to a particular time of flight are absorbed and thus decrease in number. Thereby, a content of the nuclide contained in the object can be determined according to an absorbed degree or an absorbed percentage of the photoneutrons. In other words, a weight of the nuclide contained in the object is determined based on a ratio of the quantity of the photoneutrons within the particular range of time of flight to a quantity of the photoneutrons emitted by the photoneutron emitter and corresponding to the particular range of time of flight.

Moreover, according to the method in the embodiment, the photoneutron emitter emits the photoneutrons having the predetermined range of energy at a same time. The predetermined range of energy may be a particular range corresponding to a possible substance to be detected. For example, if an object to be inspected contains a fissile nuclide such as $^{233}$U, $^{235}$U, and $^{239}$Pu, the predetermined range of energy may be 0.1-1000 eV. The predetermined range of energy may vary depending upon particular objects to be detected.

A photoneutron emitter according to an embodiment of the present invention will be described below. The photoneutron emitter can be used to identify a fissile nuclide such as $^{233}$U, $^{235}$U, and $^{239}$Pu.

Figure 5:
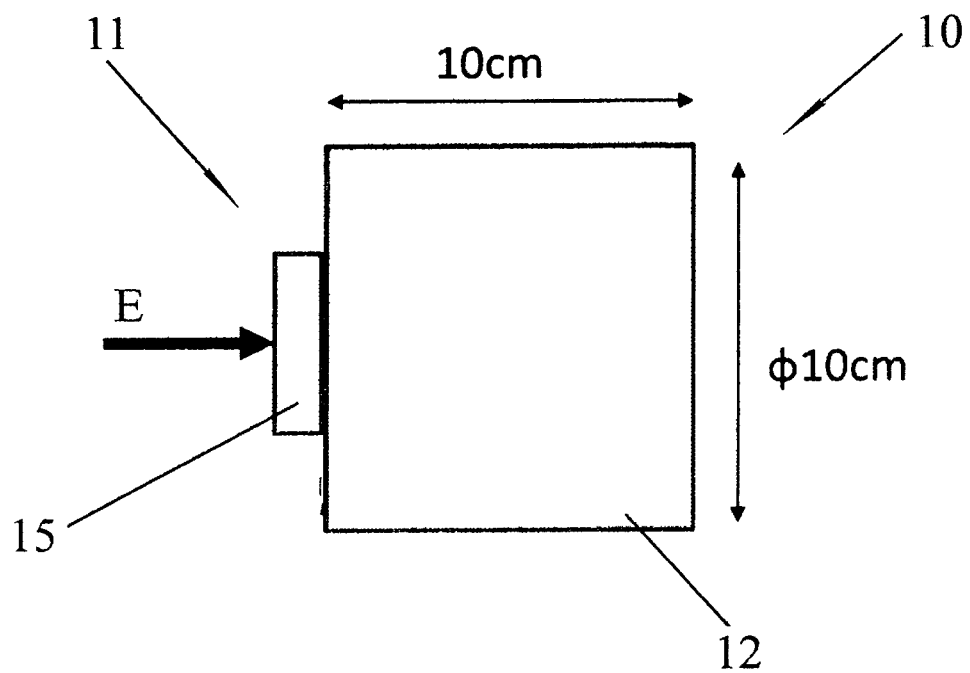
FIG. 5 is a schematic diagram of a photoneutron converting target according to an embodiment of the present invention.

As shown in FIG. 5, according to the embodiment of the present invention, a photoneutron emitter 10 for identifying a nuclide comprises: a pulsed electron accelerator 11 configured for emitting electrons; and a photoneutron converting target 12 configured to receive the electrons emitted by the pulsed electron accelerator 11 and convert the electrons into photoneutrons. The photoneutron converting target may have a volume of about 100 to about 8000 cm$^3$, of about 100 to about 2500 cm$^3$, or of about 785 cm$^3$. The photoneutron converting target 12 may be formed of heavy water or beryllium.

As shown in FIG. 5, the photoneutron converting target 12 may be a cylinder. The cylinder may have a diameter and an axial length of 5 to 20 cm, of 5 to 15 cm, of 8 to 12 cm, of 9 to 11 cm, of 9.5 to 10.5 cm, or of about 10 cm. The diameter and the axial length of the cylinder may be substantially equal to each other.

Alternatively, as shown in FIG. 5, the photoneutron converting target 12 is a cube, and an edge of the cube may have a length of 5 to 20 cm, of 5 to 15 cm, of 8 to 12 cm, of 9 to 11 cm, of 9.5 to 10.5 cm, or of about 10 cm.

Referring to FIGS. 1 and 5, the photoneutron emitter 10 may be a pulsed source. Electrons are generated by X-rays, generated by the pulsed electron accelerator 11, through the photoneutron converting target 12. Since the electron accelerator 11 operates in a pulsed mode, the electrons are generated in the pulsed mode. As a result, the departure time of the neutrons as shown in FIG. 3 can be determined.

The photoneutron converting target 12 functions to slow down the neutrons and may be formed of heavy water or beryllium. Since the heavy water has a good ability to slow down the neutrons, it can decrease the energy of the photoneutron from an order of magnitude of MeV to an order of magnitude of from keV to eV in a short time. Such a short time facilitates inverse derivation of the energies of the neutrons by means of the flight time spectrum. A heavy water cylinder having a diameter of 10 cm and a height of 10 cm is a preferable neutron target. Since a dose rate of the electron accelerator 11 can be very high, a yield of the photoneutrons can be very large, thereby ensuring an analysis speed.

A feasible design of the photoneutron target or the photoneutron converting target 12 is shown in FIG. 5. As shown in FIG. 5, firstly, an electron target 15 is bombarded with electrons E to generate X-rays, and then the X-rays react with the photoneutron converting target 12 to generate photoneutrons. The photoneutrons are slowed down while being generated. In this way, when the photoneutrons leave the photoneutron converting target 12, they will have different speeds.

Figure 6:
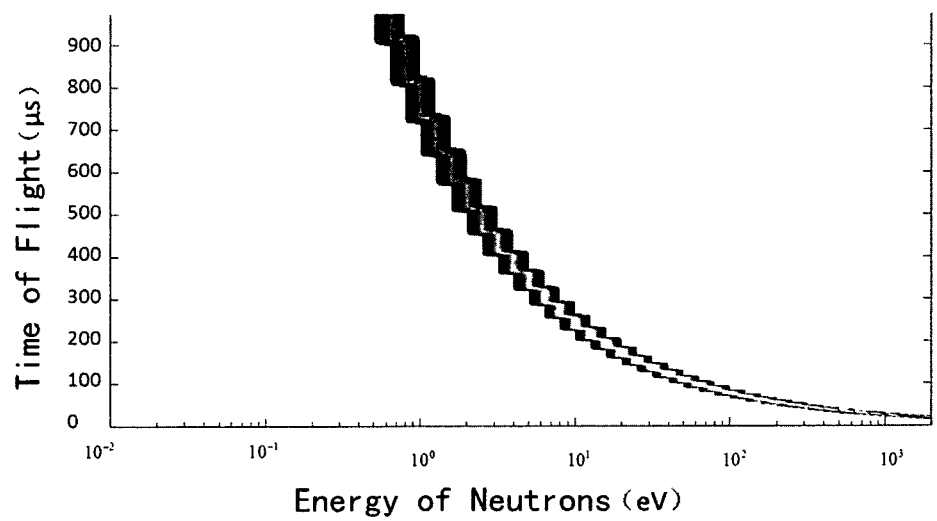
FIG. 6 is a time vs. energy distribution diagram of the photoneutron converting target according to the embodiment of the present invention.

FIG. 6 shows a time vs. energy distribution diagram of the neutrons which are emitted by the photoneutron converting target 12 and are detected by the detector. It can be seen from FIG. 6 that the detector detects the neutrons having different ranges of energy over different periods of time.

The photoneutron converting target 12 shown in FIG. 5 can be used to generate a neutron spectrum having a range of energy and a time characteristic both of which are suitable for identifying a fissile nuclide such as $^{233}$U, $^{235}$U, and $^{239}$Pu. When these neutrons penetrate an object to be inspected, resonant attenuation will occur. By a counting curve of the neutrons detected by the detector 20 at different times, it can be analyzed which nuclide causes the resonant attenuation and thus the nuclide can be identified.

The embodiments of the present invention provides a nuclide identification method, a nuclide identification system, and a photoneutron emitter for identifying a nuclide, for example, by which accuracy of identification of a nuclide is improved and practical method and system for nuclide identification are provided.

In accordance with an embodiment of the present invention, there is provided a photoneutron emitter for identifying a nuclide. The photoneutron emitter comprises: a pulsed electron accelerator configured for emitting electrons; and a photoneutron converting target configured to receive the electrons emitted by the pulsed electron accelerator and convert the electrons into photoneutrons.

In accordance with an embodiment of the present invention, the photoneutron converting target has a volume of about 100 to about 8000 cm$^3$, of about 100 to about 2500 cm$^3$, or of about 785 cm$^3$.

In accordance with an embodiment of the present invention, the photoneutron converting target is a cylinder having a diameter and an axial length of 5 to 20 cm, of 5 to 15 cm, of 8 to 12 cm, of 9 to 11 cm, of 9.5 to 10.5 cm, or of about 10 cm.

In accordance with an embodiment of the present invention, the diameter and the axial length of the cylinder are substantially equal to each other.

In accordance with an embodiment of the present invention, the photoneutron converting target is a cube, and an edge of the cube has a length of 5 to 20 cm, of 5 to 15 cm, of 8 to 12 cm, of 9 to 11 cm, of 9.5 to 10.5 cm, or of about 10 cm.

In accordance with an embodiment of the present invention, the photoneutron converting target is formed of heavy water or beryllium.

In accordance with an embodiment of the present invention, there is provided a nuclide identification method comprising the steps of: placing an object to be inspected between a photoneutron emitter and a photoneutron detector; emitting, by the photoneutron emitter, photoneutrons having a predetermined range of energy at a predetermined time;

detecting, by the photoneutron detector, a plurality of quantities of the photoneutrons which respectively fly to the photoneutron detector for different times of flight, so as to acquire a sample spectrum in which the plurality of quantities of the photoneutrons are ordered according to the different times of flight; and determining a nuclide contained in the object based on whether or not the quantity of the photoneutrons within a particular range of time of flight in the sample spectrum is lower than a predetermined value.

In accordance with an embodiment of the present invention, the nuclide identification method further comprises: provided that no object is placed, emitting, by the photoneutron emitter, photoneutrons having the predetermined range of energy at a predetermined time, and, detecting, by the photoneutron detector, a plurality of quantities of the photoneutrons which respectively fly to the photoneutron detector for different times of flight, so as to acquire a standard spectrum in which the plurality of quantities of the photoneutrons are ordered according to the different times of flight; and determining, by comparison of the sample spectrum with the standard spectrum, whether or not the quantity of the photoneutrons within the particular range of time of flight in the sample spectrum is lower than the predetermined value.

In accordance with an embodiment of the present invention, the nuclide identification method further comprises: determining a weight of the nuclide contained in the object based on a ratio of the quantity of the photoneutrons within the particular range of time of flight to a quantity of the photoneutrons emitted by the photoneutron emitter and corresponding to the particular range of time of flight.

In accordance with an embodiment of the present invention, the photoneutron emitter emits the photoneutrons having the predetermined range of energy at a same time.

In accordance with an embodiment of the present invention, the predetermined range of energy is 0.1 to 1000 eV.

In accordance with an embodiment of the present invention, the object to be inspected contains a fissile nuclide.

In accordance with an embodiment of the present invention, the photoneutron emitter comprises the abovementioned photoneutron emitter.

In accordance with an embodiment of the present invention, there is provided a nuclide identification system comprising:

a photoneutron emitter configured for emitting photoneutrons having a predetermined range of energy at a predetermined time;

a photoneutron detector configured for receiving the photoneutrons emitted by the photoneutron emitter to acquire a plurality of quantities of the photoneutrons received at respective times;

a photoneutron time-of-flight timer 40 configured for recording times of flight, of the photoneutrons emitted by the photoneutron emitter, from a time of being emitted to times of being received by the photoneutron detector; and a data processing unit 50 configured for forming a photoneutron quantity spectrum in which the plurality of quantities of the photoneutrons are ordered according to the times of flight, based on the quantity of the photoneutrons received by the photoneutron detector at every time, and the times of flight.

In accordance with an embodiment of the present invention, the nuclide identification system further comprises a comparison and determination unit 60 configured for determining a nuclide contained in an object to be inspected by comparing a quantity of the photoneutrons, within a particular range of time of flight in a photoneutron quantity spectrum acquired when the object is placed between the photoneutron emitter and the photoneutron detector, with a predetermined value.

In accordance with an embodiment of the present invention, the comparison and determination unit 60 determines whether or not the quantity of the photoneutrons within the particular range of time of flight in the photoneutron quantity spectrum acquired when the object is placed is lower than the predetermined value, by comparing the photoneutron quantity spectrum, acquired when the object is placed, with a photoneutron quantity spectrum acquired when no object is placed.

In accordance with an embodiment of the present invention, the photoneutron emitter comprises the abovementioned photoneutron emitter.

These embodiments of the present invention can improve an accuracy of identification of a nuclide, and provide a practical photoneutron emitter, method and system for identifying a nuclide. Especially, these embodiments of the present invention can improve an accuracy of identification of a fissile nuclide such as $^{233}$U, $^{235}$U, and $^{239}$Pu, and provide a practical photoneutron emitter, method and system for identifying a fissile nuclide such as $^{233}$U, $^{235}$U, and $^{239}$Pu.

The neutron detector according to the embodiments of the present invention is not limited to a particular neutron detector. In principle, it is possible for any nuclides able to capture low-energy neutrons to be used to make the detector. For example, the detector may be made of 3He, 10BF3, and the like. In addition, the nuclide identification method, the nuclide identification system, and the photoneutron emitter for identifying a nuclide according to these embodiments of the present invention may also be used to identify other nuclides.

What is claimed is:

1. A nuclide identification method, comprising:
   placing an object to be inspected between a photoneutron emitter and a photoneutron detector;
   emitting, by the photoneutron emitter, photoneutrons having a predetermined range of energy at a predetermined time;
   detecting, by the photoneutron detector, a plurality of quantities of the photoneutrons, which respectively fly to the photoneutron detector for different times of flight, so as to acquire a sample spectrum in which the plurality of quantities of the photoneutrons are ordered according to the different times of flight; and
   determining a nuclide contained in the object based on a resonant scattering energy of the nuclide by analyzing, in the sample spectrum, where a quantity of the photoneutrons within a particular range of time of flight is lower than an expected value as a result of the resonant scattering between the quantity of photoneutrons within the particular range of time of flight and the nuclide.

2. The nuclide identification method of claim 1, further comprising:
   detecting the plurality of quantities of the photoneutrons which respectively fly to the photoneutron detector for different times of flight when no object is placed between the photoneutron emitter and detector, so as to acquire a standard spectrum in which the plurality of quantities of the photoneutrons are ordered according to the different times of flight; and
   determining, by comparison of the sample spectrum with the standard spectrum, whether or not, in the sample spectrum, the quantity of the photoneutrons within the particular range of time of flight is lower than the expected value.

3. The nuclide identification method of claim 1, further comprising:
determining a weight of the nuclide contained in the object, based on a ratio of the quantity of the photoneutrons within the particular range of time of flight to a quantity of the photoneutrons emitted by the photoneutron emitter and corresponding to the same particular range of time of flight.

4. The nuclide identification method of claim 1, wherein:
the photoneutron emitter emits the photoneutrons having the predetermined range of energy at a same time.

5. The nuclide identification method of claim 4, wherein:
the predetermined range of energy is 0.1 to 1000 eV.

6. The nuclide identification method of claim 1, wherein:
the object to be inspected contains a fissile nuclide.

7. The nuclide identification method of claim 1, wherein:
the photoneutron emitter comprises:
a pulsed electron accelerator configured for emitting electrons; and
a photoneutron converting target configured to receive the electrons emitted by the pulsed electron accelerator and convert the electrons into photoneutrons.

8. A nuclide identification system, comprising:
a photoneutron emitter configured for emitting photoneutrons having a predetermined range of energy at a predetermined time;
a photoneutron detector configured for receiving the photoneutrons emitted by the photoneutron emitter to acquire a plurality of quantities of the photoneutrons received at respective times;
a photoneutron time-of-flight timer configured for recording times of flight of the photoneutrons emitted by the photoneutron emitter, from a time of being emitted to the respective times of being received by the photoneutron detector;
a data processing unit configured for forming a photoneutron quantity spectrum in which the plurality of quantities of the photoneutrons are ordered according to the times of flight; and
a comparison and determination unit configured for determining a nuclide contained in an object to be inspected based on a resonant scattering energy of the nuclide, wherein the comparison and determination unit compares a quantity of the photoneutrons within a particular range of time of flight in the photoneutron quantity spectrum with a predetermined value and determines whether the quantity of the photoneutrons within the particular range of time of flight is lower than the predetermined value as a result of the resonant scattering between the quantity of photoneutrons within the particular range of time of flight and the nuclide.

9. The nuclide identification system of claim 8, wherein:
the comparison and determination unit determines whether or not the quantity of the photoneutrons within the particular range of time of flight in the photoneutron quantity spectrum acquired when the object is placed is lower than the predetermined value, by comparing the photoneutron quantity spectrum acquired when the object is placed with a photoneutron quantity spectrum acquired when no object is placed.

10. The nuclide identification system of claim 8, wherein:
the photoneutron emitter comprises:
a pulsed electron accelerator configured for emitting electrons; and
a photoneutron converting target configured to receive the electrons emitted by the pulsed electron accelerator and convert the electrons into photoneutrons.

11. The nuclide identification system of claim 10, wherein:
the photoneutron converting target has a volume of about 100 to about 8000 $cm^3$, of about 100 to about 2500 $cm^3$, or of about 785 $cm^3$.

12. The nuclide identification system of claim 11, wherein:
the photoneutron converting target is a cylinder having a diameter and an axial length of 5 to 20 cm, of 5 to 15 cm, of 8 to 12 cm, of 9 to 11 cm, of 9.5 to 10.5 cm, or of about 10 cm.

13. The nuclide identification system of claim 11, wherein:
the photoneutron converting target is a cylinder, the cylinder having a diameter and an axial length that are substantially equal to each other.

14. The nuclide identification system of claim 11, wherein:
the photoneutron converting target is a cube, and an edge of the cube has a length of 5 to 20 cm, of 5 to 15 cm, of 8 to 12 cm, of 9 to 11 cm, of 9.5 to 10.5 cm, or of about 10 cm.

15. The nuclide identification system of claim 10, wherein:
the photoneutron converting target is a cylinder having a diameter and an axial length of 5 to 20 cm, of 5 to 15 cm, of 8 to 12 cm, of 9 to 11 cm, of 9.5 to 10.5 cm, or of about 10 cm.

16. The nuclide identification system of claim 10, wherein:
the photoneutron converting target is a cylinder, the cylinder having a diameter and an axial length that are substantially equal to each other.

17. The nuclide identification system of claim 10, wherein:
the photoneutron converting target is a cube, and an edge of the cube has a length of 5 to 20 cm, of 5 to 15 cm, of 8 to 12 cm, of 9 to 11 cm, of 9.5 to 10.5 cm, or of about 10 cm.

18. The nuclide identification system of claim 10, wherein:
the photoneutron converting target is formed of heavy water or beryllium.

* * * * *